United States Patent [19]

Munck et al.

[11] Patent Number: 4,736,752

[45] Date of Patent: Apr. 12, 1988

[54] TRANSCUTANEOUS MEDICAL ELECTRODE

[75] Inventors: Gary Munck, Fallbrook; Jens Axelgaard, Costa Mesa; Theodore Grussing, Huntington Beach, all of Calif.

[73] Assignee: Axelgaard Manufacturing Co., Ltd., Fallbrook, Calif.

[21] Appl. No.: 935,973

[22] Filed: Nov. 28, 1986

[51] Int. Cl.⁴ ............................................. A61N 1/04
[52] U.S. Cl. .................................... 128/798; 128/802
[58] Field of Search ............... 128/798, 802, 803, 640, 128/641

[56] References Cited

U.S. PATENT DOCUMENTS

| | | | |
|---|---|---|---|
| 1,989,282 | 1/1935 | Kimble et al. | 128/798 |
| 3,464,404 | 9/1969 | Mason | 128/2.06 |
| 3,518,984 | 7/1970 | Mason | 128/2.06 |
| 4,082,087 | 4/1978 | Howson | 128/2.06 |
| 4,166,465 | 9/1979 | Esty et al. | 128/303.13 |
| 4,213,463 | 7/1980 | Osenkarski | 128/639 |
| 4,243,051 | 1/1981 | Witteman | 128/798 |
| 4,257,424 | 3/1981 | Cartmell | 128/641 |
| 4,353,373 | 10/1982 | Sessions et al. | 128/641 |
| 4,367,755 | 1/1983 | Barley | 128/798 |
| 4,391,278 | 7/1983 | Cahalen et al. | 128/640 |
| 4,422,461 | 12/1983 | Glumac | 128/798 |
| 4,458,696 | 7/1984 | Larimore | 128/798 |
| 4,522,211 | 6/1985 | Bare et al. | 128/640 |

Primary Examiner—Lee S. Cohen
Attorney, Agent, or Firm—Walter A. Hackler

[57] ABSTRACT

A transcutaneous medical electrode is provided for coupling electrical energy into nerves and/or muscles for the stimulation thereof. The electrode uses an array of conductive ink patterns in combination with a conductive adhesive to provide power coupling in which the current density across the electrode can be preselected by ink design for use on specific curvaceous areas of a body to transcutaneously stimulate muscle and/or nerves.

25 Claims, 1 Drawing Sheet

TRANSCUTANEOUS MEDICAL ELECTRODE

The present invention generally relates to transcutaneous electrodes and, more particularly, to medical electrodes employed in the transcutaneous stimulation of nerves and muscles. Transcutaneous electrical nerve stimulation is useful in post-operative and chronic pain control. Electrical muscle stimulation has been found useful in maintaining and developing muscle tissue. Stimulating electrodes of this type must provide for electrical distribution of current over a large area for long periods of time, for example, days, weeks or even months.

The electrode must be useful over many areas of the body in order to be effective for the many hundreds of muscles in the body which may benefit from the electrical stimulation. Hence, it can be appreciated that the electrodes may be applied to rather broad areas of the body, such as the legs, or arms, and also be applied to comparatively curvaceous areas of the body, such as the hands, in which the electrodes may be placed over a knuckle or around a finger.

Because of the curved nature of the epidermis layer onto which the electrodes is to be applied in order to stimulate underlying muscles, effective coupling of the electrode to the responding muscle can be best effected by adjusting the current density and distribution across the surface of the transcutaneous medical electrode. Many prior art stimulating electrodes have insufficient flexibility to move with the user's skin during the contraction of the muscle being stimulated which can, over a period of time, cause severe irritation and rash to the user's skin. In addition, the prior art electrodes have not provided appropriate current distribution for this stimulation of muscle and, in many instances, caused hot or burned spots on the individual's skin from the electrode's stimulation.

Another factor relating to the usefulness of stimulation electrode is its cost. Heretofore many electrodes have been manufactured utilizing very complex configurations and compositions including woven materials, wire meshes, gauzes saturated with electrolites, and other combinations which have been costly to produce. In many instances, where the electrode is utilized over a longer period of time, such as in connection with sports injuries, electrodes have been designed to last for long periods of time. Unfortunately, the desire for producing an extremely long life electrode has unduly complicated the electrode configuration.

Another important factor in the use of the electrode over a period of time is the thickness of the electrode. It should be appreciated that bulky, thick, molded type electrodes are not as flexible and have limited use since they cannot be conformed to curvaceous areas of the body. Since these electrodes do not have a very low profile, they make the wearing thereof uncomfortable and unsuitable for use under clothing, or bandages, and the like.

As hereinbefore mentioned, a useful transcutaneous stimulation electrode must be able to flex, and/or stretch, in order to accommodate skin movement during treatment. While this is occurring, however, the conductivity of the electrode should not be interrupted, or distorted, due to the stretching of the electrode. In addition to providing uniform conductivity, it must be appreciated that the electrode should be one in which the current density thereacross is appropriate for the muscles being stimulated, as well as the overlying curvaceous skin.

Heretofore, many stimulation electrodes have typically utilized a uniform mesh, or grid, of conductive material. Some have employed conductive ink disposed on a plastic-like sheet, such as disclosed in U.S. Pat. No. 4,522,211 to Bare, et al. As shown in the hereinabove-referenced U.S. Patent, conductive ink may be disposed on a plastic backing layer and coupled to the skin through a conductive adhesive. This type of electrode is concerned with the monitoring of biological or physiological electrical potential associated with muscular activity. It is not concerned with, or effective for, coupling electrical energy or current into the body muscles or nerves in order to stimulate them. Monitoring electrodes do not address the problem of current density since there is no need to couple electrical current subcutaneously. Hence, a monitoring electrode is not suited to transcutaneous stimulation of muscles and nerves.

Another significant difference between monitoring electrodes and power coupling electrodes for muscle and/or nerve stimulation is that the former are passive devices and the latter are active devices. That is, the power coupling electrodes cause muscle contraction and relaxation which causes movement of the body and skin. In order to accommodate this movement, the active electrode must flex with the skin in order not to cause abrasion and to maintain continuity of electrical current through the skin. The passive electrode merely receives signals which do not cause, or result from, skin movement.

The present invention provides for a power coupling electrode in which the current density thereacross can be designed for use of the electrode on specific curvaceous areas on a body to transcutaneously stimulate muscles and/or nerves.

SUMMARY OF THE INVENTION

A transcutaneous medical electrode in accordance with the present invention generally includes a flexible backing sheet and an electrical conductor disposed along the periphery of the backing sheet. Conductive grid means are provided which are connected with the electrical conductor at a plurality of preselected points for coupling electrical energy through a user's skin. The conductive grid means includes an array of discrete electrical conductors with non-conductive areas therebetween. This important feature of the present invention enables the coupling of a preselected current distribution with the skin by varying both the spacing of the electrical conductors and the thickness thereof. The current distribution can be further modified by using electrical conductors of different thicknesses.

Insulation means may provide for preventing outside electrical contact with the electrical conductor disposed along the backing sheet periphery. This feature enables the conductive grid means to be fed with current from a source which is not coupled with the skin. In this manner, the current density toward the outside, or periphery, of the transcutaneous medical electrode can be controlled.

Additionally, means are provided for connecting outside power source to the electrical conductor disposed along the periphery of the backing sheet and a conductive adhesive is disposed on the backing sheet and the conductive grid means for electrically coupling the conductive grid means to a user's skin.

More specifically, the conductive grid means, as well as the electrical conductor disposed along the periphery of the backing sheet, may comprise an electrically conductive ink disposed on the flexible backing sheet. This feature not only reduces the overall cost of the electrode, but also enables the electrode to have a very thin cross-section, or low profile.

The means for connecting an outside power source to the electrical conductor disposed along the periphery of the backing sheet may consist of an elongated portion of the backing sheet having conductive ink thereon in contact with the conductive ink disposed along the periphery of the backing sheet. In this manner, electrical contact is made through the peripheral electrical conductor to the conductive grid means without the use of bulky fasteners, which may otherwise cause the electrode to be uncomfortable for wear over long periods of time, or distort the current density across the electrode.

The insulation means includes a flexible non-conductive sheet having an aperture therein for enabling the stretchable non-conductive sheet to cover both the electrical conductor disposed along the periphery of the backing sheet and the conductive ink on the backing sheet elongated portion, while not covering the conductive grid means, the latter being coupled through the aperture, or window, to a user's skin via the conductive adhesive means. The flexible non-conductive sheet also functions as a means for facilitating removal and positioning of the transcutaneous medical electrode on a user's skin. Since the conductive adhesive adheres to the user's skin only through the aperture, the periphery of the electrode can be easily separated from the user's skin and used as a flap to remove the electrode without touching the conductive adhesives. In this manner, the conductive adhesive is less likely to be torn or separated from the backing sheet.

In order to control the current density, the conductive grid means comprises a network pattern of conductive ink disposed on the stretchable backing sheet and interconnected with the electrical conductive ink disposed along the periphery of the backing sheet by a plurality of conductive ink ribbons. One network may comprise a plurality of concentric conductive ink circles interconnected with one another and to the conductive ink on the periphery of the backing sheet by a plurality of conductive ink ribbons disposed along radii of the concentric ink circles.

Further providing means for creating a preselected current density within the periphery of the backing sheet includes disposing the concentric conductive ink circles with varying widths and spacing therebetween.

Another pattern which the conductive grid means may take is a rectangular mesh of conductive ink ribbons disposed on the stretchable backing sheet and into the conductive ink disposed along the periphery of the backing sheet.

BRIEF DESCRIPTION OF THE DRAWINGS

The advantages and features of the present invention will appear from the following description, considered in conjunction with the accompanying drawings, in which.

DETAILED DESCRIPTION

Figure 1:
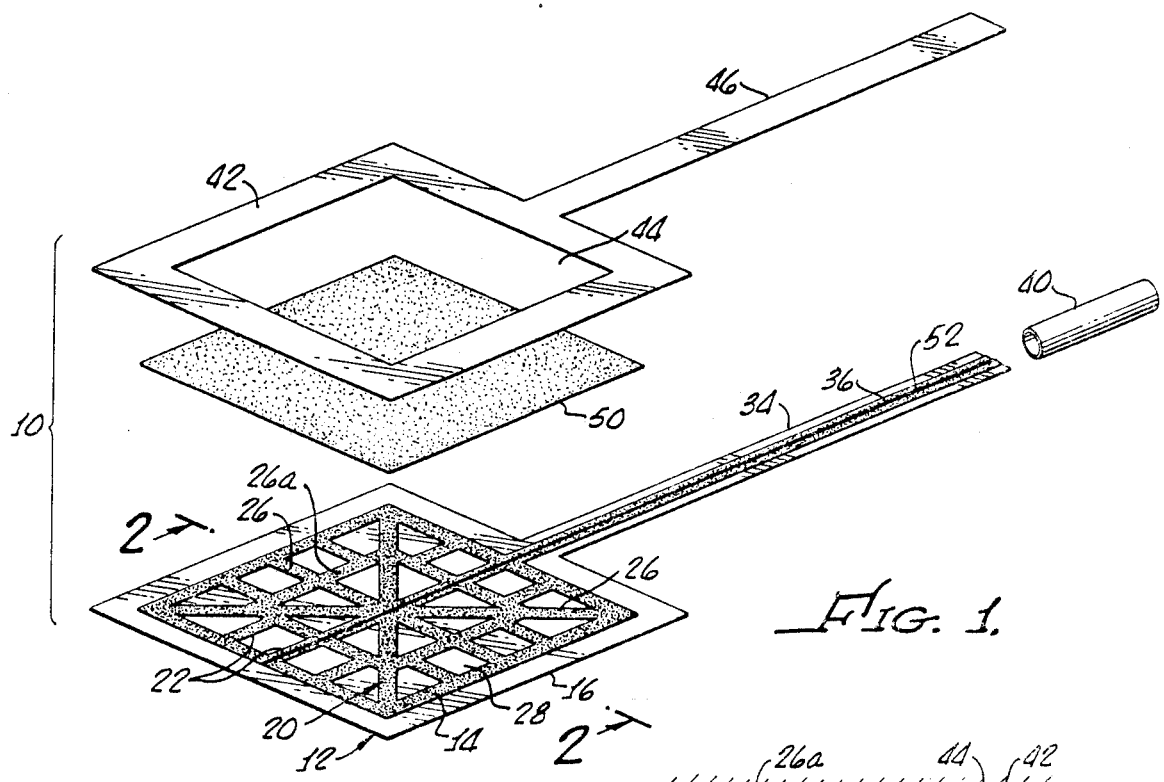
FIG. 1 is an exploded perspective view of a transcutaneous medical electrode made in accordance with the present invention, generally showing a flexible non-conductive backing sheet, an electrical conductor disposed along the periphery of the backing sheet along with a lead portion extending along the elongated portion of the backing sheet, and a flexible non-conductive frame having a window therein for enabling a conductive adhesive applied onto the conductive ink to couple electrical energy from the conductive ink pattern to a user's skin.
Figure 2:
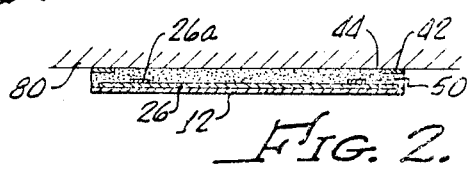
FIG. 2 is a cross-section of the transcutaneous electrode shown in FIG. 1, taken along line 2—2, shown conductors having differing thicknesses in order to achieve a preselected current density.
Figure 3:
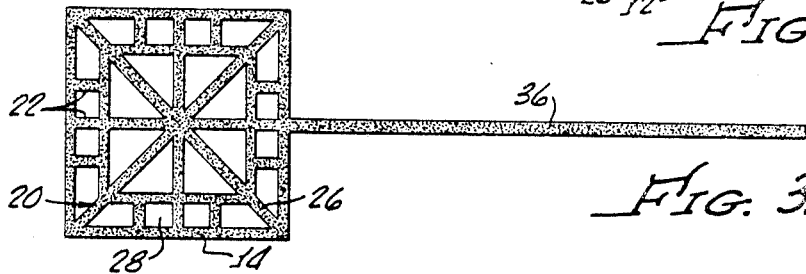
FIG. 3 is a diagram showing one embodiment of the conductive grid means.

Turning now to FIGS. 1, 2 and 3, there is shown a transcutaneous medical electrode 10, constructed in accordance with the present invention, having a flexible backing sheet 12 with an electrical conductor 14 disposed along a periphery 16 of the backing sheet. A conductive grid 20 disposed on the flexible backing sheet includes a conductive ink pattern 22, which consists of an array of discrete electrical connectors 26 having non-conductive areas 28 of the backing sheet 12 therebetween. The backing sheet 12 may be formed from a sheet of 3 mil polyethylene, or the like.

To provide for a lead to the conductive ink 14 on the periphery 16 of the backing sheet 12, the backing sheet may include an elongated portion 34 with conductive ink 36 printed thereon and communicating with the ink 14 on the periphery 16. Further connection to a power source, not shown, may be provided by a conventional crimped connector 40 which may be squeezed onto the conductive ink 36.

A flexible polyethylene frame 42 having an aperture, or window 44, and a tail portion 46 of equal size and length as the elongated portion 34 of the backing sheet 12 provides a means for insulating outside electrical contact with the ink 14 on the periphery 16 of the backing sheet 12. The polyethylene frame is glued in position by a flexible conductive adhesive 50 which is disposed onto the conductive ink pattern 22 and over the ink 14 on the periphery 16. It has been found that a suitable conductive adhesive is one such as that manufactured by Valleylab, Inc., of Boulder, Colo., under the name PolyHesive. This particular adhesive has the advantage of being flexible so that it will move with the user's skin and the flexible backing sheet without losing contact therebetween, or interrupting the electrical signals transmitted therethrough.

The tail portion 46 may be glued to the elongated portion 34 and conductive 36 in any conventional manner. In addition, a reinforcing strand, or filament, 52 of any suitable type, which may be conductive or non-conductive, may be glued to or embedded in the ink 36, or elongated portion 34 in order to provide greater strength to the elongated portion and overlying tail portion 46. This feature reduces the possibility of rupture of the conductive ink 36 due to handling thereof.

Importantly, the conductive adhesive is overlayed onto the peripheral ink 14 in order to ensure continuity. That is, the conductive adhesive disposed over the ink and under the frame 42 enables greater flexibility of the periphery 16 of the backing sheet in that any discontinuities occurring in the conductive ink are bypassed by the conductive adhesive 50.

Hence, the conductive adhesive acts in combination with the conductive ink to create a current density that is resistant to distortion by the rupture of individual connectors 26 which may occur over long term use of the electrode by the flexing thereof with the activity associated with muscle and/or nerve stimulation.

Suitable conductive inks for use in the present invention include conductive metals and carbon carried by a suitable binder which may be applied in any suitable conventional manner. However, other conductive mediums such as laminates of metal foil and combinations of conductive ink and binder layers may be used to vary the thickness of the conductive grid 20 (see FIG. 2), in order to achieve a preselected current density. In this manner, an individual connector 26a, being of greater thickness, can have a lower resistance than other connectors 26, hence, carry a greater current and thereby alter the current density across the electrode 10. Specifically, connectors 26a, having greater thickness, may be selected and arranged according to the application intended for the electrode 10, i.e., for use on knuckles, body limbs or torso, which can be determined on an empirical basis.

The width of the individual connectors 26 can be selected to design an appropriate current density for the muscles to be stimulated and can vary widely. However, it has been found that line widths between about one millimeter and about three millimeters are useful, depending upon the overall current density required and the overall size of the electrode which may have dimensions measured from about one centimeter to about thirty or more centimeters.

It should be appreciated that the conductive ink has a higher conductivity than the adhesive, nonetheless, the adhesive 50 provides a backup role for discontinuities occurring in the conductive ink during use of the electrode in which some of the individual lines of ink may be ruptured because of stretching of the electrode.

Figure 4:
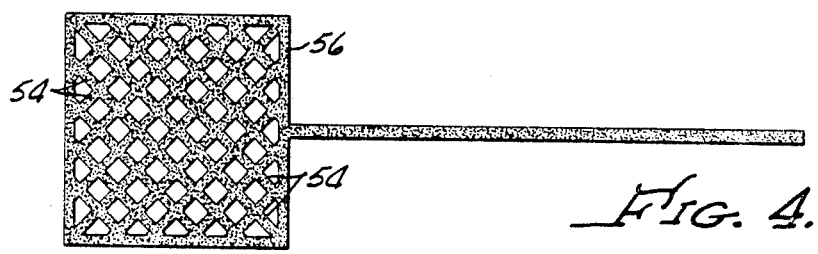
FIG. 4 is a diagram of another embodiment of a conductive grid means.

A number of patterns for the conductive ink 14 may be utilized depending upon the size of the electrode and the nature of its application. For example, for a more uniform current density electrode suitable for broad areas, a pattern such as that shown in FIG. 4 may be utilized, which consists of a rectangular mesh 54 between a peripheral conductor 56, whereas a more contoured current density is desired as with an electrode design for a contoured portion of the body, such as knuckles and fingers and the like, and as shown in FIGS. 1 or 5 may be utilized.

Figure 5:
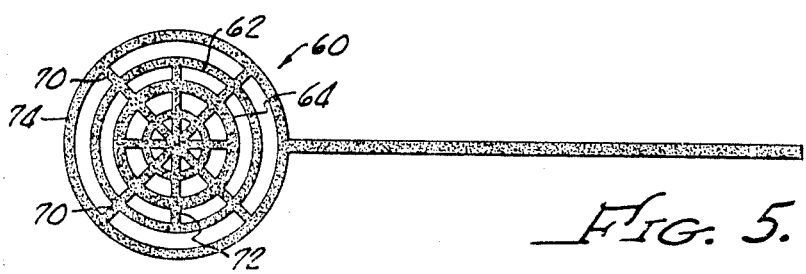
FIG. 5 is yet another diagram of an embodiment of the grid means by which the current density of the electrode can be controlled by varying the width of the conductive ink.

In FIG. 5, the conductive grid 60 may include a plurality of concentric conductive ink circles 62, 64, interconnected by a plurality of conductive ink ribbons 70, 72. By varying the number of concentric circles and the width thereof, as shown by the circle 64 and the spacing, proper current density can be achieved. In addition, the current density towards the outside of the electrode may be controlled by limiting the number of ribbons 70 which contact the ink 74 on the periphery of the electrode.

It should be appreciated that in terms of the conductivity of the electrode, the peripheral ink 14, 56, 74 (FIGS. 1, 4 and 5, respectively) is not coupled to a user's skin as closely as the connectors 26 because of the frame disposed therebetween. This significantly reduces edge effects of the electrode which may occur by having a rapid change in current density near the edge of the electrode which can be undesirable because of the development of hot spots at these locations which result in discomfort to the user and possible skin irritation.

As hereinbefore pointed out, the flexible non-conductive sheet 42 acts as a cover sheet for facilitating removal and positioning of the transcutaneous medical electrode on a user's skin 80, (see FIG. 2).

Since the conductive adhesive 50 sticks to the user's skin 80 only through the apparatus 44, the sheet 42 is not bound to the skin 80 and acts as a flap to facilitate separation of the electrode 10 from the skin. Hence, the sheet 42 prevents damage to the adhesive 50 which might otherwise occur by direct handling thereof, as would be necessary to peel the electrode from the skin if the sheet 42 were not present.

Although there has been described hereinabove a specific transcutaneous medical electrode, in accordance with the present invention for the purpose of illustrating the manner in which the invention may be used to advantage, it should be appreciated that the invention is not limited thereto. Accordingly, any and all modifications, variations or equivalent arrangements which may occur to those skilled in the art, should be considered to be within the scope of the invention as defined in the appended claims.

What is claimed is:

1. A transcutaneous medical electrode comprising: a flexible backing sheet;
   an electrical conductor disposed along the periphery of the backing sheet;
   conductive grid means connected with the electrical conductor at a plurality of preselected points, for coupling electrical energy through a user's skin, said conductive grid means comprising an array of discrete electrical conductors with non-conductive areas therebetween;
   means for connecting an outside power source to said electrical conductor disposed along the periphery of the backing sheet; and
   conductive adhesive means disposed on the backing sheet and conductive grid means for electrically coupling the conductive grid means to a user's skin.

2. The transcutaneous medical electrode according to claim 1 wherein the conductive grid means includes means for creating a preselected current density within the periphery of the backing sheet.

3. The transcutaneous medical electrode according to claim 2 wherein the means for creating a preselected current density within the periphery of the backing sheet comprises an array of discrete electrical conductors having varying widths and spacing therebetween.

4. The transcutaneous medical electrode according to claim 3 wherein the means for creating a preselected current density within the periphery of the backing sheet comprises an array of discrete electrical conductors having varying thicknesses.

5. A transcutaneous medical electrode comprising:
   a flexible backing;
   an electrical conductor disposed along the periphery of the backing sheet;
   conductive grid means connected with the electrical conductor at a plurality of preselected points, for coupling electrical energy through a user's skin, said conductive grid means comprising an array of discrete electrical conductors with non-conductive area therebetween;

insulation means for preventing outside electrical contact with the electrical conductor disposed along the backing sheet periphery;

means for connecting an outside power source to said electrical conductor disposed along the periphery of the backing sheet; and conductive adhesive means disposed on the backing sheet and conductive grid means for electrically coupling the conductive grid means to a user's skin.

6. The transcutaneous medical electrode according to claim 5 wherein the electrical conductor disposed along the periphery of the backing sheet and the discrete electrical conductors comprise an electrically conductive medium disposed on said flexible backing sheet.

7. The transcutaneous medical electrode according to claim 6 wherein the electrical medium comprises a conductive ink.

8. The transcutaneous medical electrode according to claim 7 wherein the means for connecting an outside power source to said electrical conductor disposed along the periphery of the backing sheet comprises an elongated portion of the backing sheet having conductive ink thereon in contact with the conductive ink disposed along the periphery of the backing sheet.

9. The transcutaneous medical electrode according to claim 8 wherein the insulation means comprises a flexible nonconductive sheet having an aperture therein for enabling the flexible nonconductive sheet to cover both the electrical conductive disposed along the periphery of the backing sheet and the conductive ink on the backing sheet elongated portion while not covering the conductive grid means.

10. The transcutaneous medical electrode according to claim 9 wherein the conductive grid means comprises a network pattern of conductive ink disposed on said flexible backing sheet and interconnected with the electrical conductor disposed along the periphery of the backing sheet by a plurality of conductive ink ribbons.

11. The transcutaneous medical electrode according to claim 10 wherein the network pattern comprises concentric circles and the conductive ink ribbons are disposed along radii of the concentric conductive ink circles.

12. The transcutaneous medical electrode according to claim 10 wherein the network pattern comprises a rectangular mesh.

13. A transcutaneous medical electrode comprising:
a flexible non-conductive backing sheet having an elongated lead portion;
conductive ink disposed in an electrically continuous manner along a periphery of the backing sheet and along the lead portion thereof;
conductive grid means, interconnecting the conductive ink disposed on the flexible backing sheet periphery, for producing a preselected current density over an area inside the flexible backing sheet periphery, said conductive grid means comprising an array of conductive ink lines of preselected width disposed on said flexible backing sheet with non-conductive areas therebetween;
cover sheet means comprising a flexible non-conductive material disposed over said conductive ink on the periphery of the flexible backing sheet for facilitating removal and positioning of the transcutaneous medical electrode on a user's skin; and
conductive adhesive means disposed on the backing sheet and conductive grid means within the flexible backing sheet periphery for electrically coupling the conductive grid means to a user's skin.

14. The transcutaneous medical electrode according to claim 13 wherein the conductive grid means comprises a network pattern of conductive ink interconnected with the conductive ink disposed along the periphery of the backing sheet by a plurality of conductive ink ribbons.

15. The transcutaneous medical electrode according to claim 14 wherein the network pattern comprises concentric circles and the conductive ink ribbons are disposed along radii of the concentric conductive ink circles.

16. The transcutaneous medical electrode according to claim 15 wherein conductive grid means comprises a plurality of conductive ink concentric circles having varying widths, thicknesses and spacing therebetween for creating a preselected current density.

17. The transcutaneous medical electrode according to claim 14 wherein the network pattern comprises a rectangular mesh.

18. A transcutaneous medical electrode comprising:
a flexible backing sheet;
an electrical conductor disposed along the periphery of the flexible backing sheet;
conductive grid means connected with the electrical conductor at a plurality of preselected points, for producing a preselected current density over an area inside the flexible backing sheet periphery, said conductive grid means comprising an array of discrete electrical conductors with nonconductive areas therebetween;
insulation means for preventing outside electrical contact with the electrical conductor disposed along the backing sheet periphery;
means for connecting an outside power source to said electrical conductor disposed along the periphery of the backing sheet; and
conductive adhesive means disposed on the backing sheet and conductive grid means for both electrically coupling the conductive grid means to a user's skin, and for maintaining electrical conductivity along the discrete electrical conductors.

19. The transcutaneous medical electrode according to claim 18 wherein the electrical conductor disposed along the periphery of the backing sheet and the discrete electrical conductors comprises an electrically conductive ink disposed on said flexible backing sheet.

20. The transcutaneous medical electrode according to claim 19 wherein the means for connecting an outside power source to said electrical conductor disposed along the periphery of the backing sheet comprises an elongated portion of the backing sheet having conductive ink thereon in contact with the conductive ink disposed along the periphery of the backing sheet.

21. The transcutaneous medical electrode according to claim 20 wherein the insulation means comprises a flexible non-conductive sheet having an aperture therein for enabling the flexible non-conductive sheet to cover both the electrical conductor disposed along the periphery of the backing sheet and the conductive ink on the backing sheet elongated portion while not covering the conductive grid means.

22. The transcutaneous medical electrode according to claim 21 wherein the conductive grid means comprises a network pattern of conductive ink disposed on said flexible backing sheet and interconnected with the electrical conductor disposed along the periphery of the backing sheet by a plurality of conductive ink ribbons.

23. The transcutaneous medical electrode according to claim 22 wherein the network pattern comprises concentric circles and the conductive ink ribbons are disposed along the radii of the concentric conductive ink circles.

24. The transcutaneous medical electrode according to claim 23 wherein the conductive grid means comprises a plurality of conductive ink concentric circles having varying widths of thicknesses and spacing therebetween for creating a preselected current density.

25. The transcutaneous medical electrode according to claim 18 wherein the conductive grid means comprises a rectangular mesh of conductive ink ribbons disposed on said flexible backing sheet and interconnected with one another and to the electrical conductor disposed along the backing sheet periphery.

* * * * *